United States Patent
Chudova

(10) Patent No.: US 11,193,175 B2
(45) Date of Patent: Dec. 7, 2021

(54) NORMALIZING TUMOR MUTATION BURDEN

(71) Applicant: GUARDANT HEALTH, INC., Redwood City, CA (US)

(72) Inventor: Darya Chudova, San Jose, CA (US)

(73) Assignee: GUARDANT HEALTH, INC., Redwood City, CA (US)

(*) Notice: Subject to any disclaimer, the term of this patent is extended or adjusted under 35 U.S.C. 154(b) by 0 days.

(21) Appl. No.: 16/866,229

(22) Filed: May 4, 2020

(65) Prior Publication Data

US 2020/0263260 A1 Aug. 20, 2020

Related U.S. Application Data

(63) Continuation of application No. PCT/US2018/059068, filed on Nov. 2, 2018.

(60) Provisional application No. 62/581,563, filed on Nov. 3, 2017.

(51) Int. Cl.
| | |
|---|---|
| *G16B 20/00* | (2019.01) |
| *G16H 50/30* | (2018.01) |
| *G16B 20/20* | (2019.01) |
| *C12Q 1/6886* | (2018.01) |

(52) U.S. Cl.
CPC ........... *C12Q 1/6886* (2013.01); *G16B 20/00* (2019.02); *G16B 20/20* (2019.02); *G16H 50/30* (2018.01); *C12Q 2600/112* (2013.01); *C12Q 2600/156* (2013.01)

(58) Field of Classification Search
CPC ....... G16H 50/30; G16B 20/20; C12Q 1/6886
See application file for complete search history.

(56) References Cited

U.S. PATENT DOCUMENTS

| | | | |
|---|---|---|---|
| 6,582,908 | B2 | 6/2003 | Fodor et al. |
| 7,537,898 | B2 | 5/2009 | Bost et al. |
| 9,598,731 | B2 | 3/2017 | Talasaz |
| 9,792,403 | B2 | 10/2017 | Sun et al. |
| 2001/0053519 | A1 | 12/2001 | Fodor et al. |
| 2002/0110538 | A1 | 8/2002 | Mathiowitz et al. |
| 2011/0160078 | A1 | 6/2011 | Fodor et al. |
| 2014/0214579 | A1 | 7/2014 | Shen et al. |
| 2015/0051088 | A1 | 2/2015 | Kim |
| 2016/0032396 | A1 | 2/2016 | Diehn et al. |
| 2016/0110497 | A1* | 4/2016 | Dzakula ............... G06F 17/18 702/20 |
| 2016/0326597 | A1 | 11/2016 | Chan et al. |
| 2017/0073774 | A1 | 3/2017 | Lo et al. |
| 2017/0267760 | A1 | 9/2017 | Diaz et al. |
| 2018/0282417 | A1 | 10/2018 | Higgs et al. |
| 2018/0363066 | A1 | 12/2018 | Chalmers et al. |
| 2018/0371099 | A1 | 12/2018 | Bourgon et al. |
| 2019/0025308 | A1 | 1/2019 | Cummings et al. |
| 2019/0085403 | A1 | 3/2019 | Frampton et al. |
| 2019/0169685 | A1 | 6/2019 | Georgiadis et al. |
| 2019/0219586 | A1 | 7/2019 | Fabrizio et al. |
| 2020/0032323 | A1 | 1/2020 | Talasaz et al. |
| 2020/0258601 | A1 | 8/2020 | Lau |

FOREIGN PATENT DOCUMENTS

| | | |
|---|---|---|
| WO | 2013190441 A2 | 12/2013 |
| WO | 2014039556 A1 | 3/2014 |
| WO | 2016081947 A2 | 5/2016 |
| WO | 2016145578 A1 | 9/2016 |
| WO | 2017151517 A1 | 9/2017 |
| WO | 2017151524 A1 | 9/2017 |
| WO | 2019060640 A1 | 3/2019 |
| WO | 2019211418 A1 | 11/2019 |

OTHER PUBLICATIONS

Bennett et al. Cell-free DNA and next-generation sequencing in the service of personalized medicine for lung cancer. Oncotarget 2016, vol. 7, No. 43, pp. 71013-71035 (Year: 2016).*
Goodman et al. Tumor Mutational Burden as an Independent Predictor of Response to Immunotherapy in Diverse Cancers. Mol Cancer Ther 2017, vol. 16, No. 11, pp. 2598-2608; published online Aug. 23, 2017 (Year: 2017).*
Cornish et al. A comparison of variant calling pipelines using genome in a bottle as a reference. Biomedical Research International 2015, pp. 1-11 (Year: 2015).*
Chalmers, Z.R. et al. "Analysis of 100,000 human cancer genomes reveals the landscape of tumor mutational burden" Genome Med (2017) 9:34.
Champiat, S. et al. "Exomics and Immunogenics: Bridging mutational load and immune checkpoints efficacy" OncoImmunology (2014) 3:327817 (6 pages).
Gandara, D.R. et al. "Blood-based tumor mutational burden as a predictor of clinical benefit in non-small-cell lung cancer patients treated with atezolizumab" Nature Med (2018) 24:1441-1448 and Supplemental Information.
Hellmann, M.D. et al. "Genomic Features of Response to Combination Immunotherapy in Patients with Advanced Non-Small-Cell Lung Cancer" Cancer Cel (2018) 33:843-852.
Li, H. "Aligning sequence reads, clone sequences and assembly contigs with BWA-MEM" (2013) arXiv:1303.3997.
Mcgranahan, N. et al. "Clonal neoantigens elicit T cell immunoreactivity and sensitivity to immune checkpoint blockade" Science (2016) 25(251):1463-1469.
Pardoll, D.M. "The blockade of immune checkpoints in cancer immunotherapy" Nature Rev Cancer (2012) 12:252-264.

(Continued)

*Primary Examiner* — Olivia M. Wise
(74) *Attorney, Agent, or Firm* — Timothy A. Hott

(57) ABSTRACT

Values for tumor mutation burden from different samples can be made more comparable to each other or control standards by a normalization regime that takes into account the minor allele fraction of highly rated mutations in a sample. Such analysis can provide an indication where the tumor mutation burden of a test sample lies on a distribution of tumor mutation burdens in a control population, and thus, whether the individual providing the test sample is likely to be amenable to immunotherapy to treat cancer.

30 Claims, 2 Drawing Sheets

(56) References Cited

OTHER PUBLICATIONS

Rizvi, H. et al. "Molecular Determinants of Response to Anti-Programmed Cell Death (PD)-1 and Anti-Programmed Death-Ligand 1 (PD-L1) Blockade in Patients With Non-Small-Cell Lung Cancer Profiled With Targeted Next-Generation Sequencing" J. Clin Oncology (2018) 36(7):633-641 and Appendix.

Rizvi, N.A. et al. "Mutational landscape determines sensitivity to PD-1 blockade in non-small cell lung cancer" Science (2015) 348:124-128.

Rosenberg, J.E. et al. "Atezolizumab in patients with locally advanced and metastatic urothelial carcinoma who have progressed following treatment with platinum-based chemotherapy: a single-arm, multicentre, phase 2 trial" Lancet (2016) 387(10031): 1909-1920.

Siravegna, G. et al. "Integrating liquid biopsies into the management of cancer" Nature Reviews Clinical Oncology (2017) 14:531-548.

Snyder, A. et al. "Genetic Basis for Clinical Response to CTLA-4 Blockade in Melanoma" NEJM (2014) 371 (23):2189-2199.

Vanderwalde, A. et al. "Microsatellite instability status determined by next-generation sequencing and compared with PD-L1 and tumor mutational burden in 11,348 patients" Cancer Medicine (2018) 7(3):746-756.

Lipson, E.J. et al. "Circulating tumor DNA analysis as a real-time method for monitoring tumor burden in melanoma patients undergoing treatment with immune checkpoint blockade" J ImmunoTherapy of Cancer (2014) 2:42 (7 pages).

Chan, K.C. et al.; "Cancer Genome Scanning in Plasma: Detection of Tumor-Associated Copy Number Aberrations, Single-Nucleotide Variants, and Tumoral Heterogeneity by Massively Parallel Sequencing"; Clinical Chemistry; 2013 (Epub Oct. 11, 2012); vol. 59, No. 1; pp. 211224.

Extended European search report and opinion for 18872946.1, dated Jul. 14, 2021.

International Search Report and Written Opinion dated Jan. 17, 2019 for PCT/US2018/059068.

\* cited by examiner

NORMALIZING TUMOR MUTATION BURDEN

CROSS-REFERENCE

This application is a continuation of International Patent Application No. PCT/US2018/059068, filed Nov. 2, 2018, which claims priority to U.S. Provisional Application No. 62/581,563, filed on Nov. 3, 2017, which application is entirely incorporated herein by reference for all purposes.

BACKGROUND

A tumor is an abnormal growth of cells. Fragmented DNA is often released into bodily fluid when cells, such as tumor cells, die. Thus, some of the cell-free DNA in body fluids is tumor DNA. A tumor can be benign or malignant. A malignant tumor is often referred to as a cancer.

Cancer is a major cause of disease worldwide. Each year, tens of millions of people are diagnosed with cancer around the world, and more than half eventually die from it. In many countries, cancer ranks as the second most common cause of death following cardiovascular diseases. Early detection is associated with improved outcomes for many cancers.

Cancer is usually caused by the accumulation of mutations within an individual's normal cells, at least some of which result in improperly regulated cell division. Such mutations commonly include single nucleotide variations (SNVs), gene fusions, insertions and deletions (indels), transversions, translocations, and inversions. The number of mutations within a cancer is an indicator of the cancers susceptibility to immunotherapy.

Cancers are often detected by biopsies of tumors followed by analysis of cell pathologies, biomarkers or DNA extracted from cells. But more recently it has been proposed that cancers can also be detected from cell-free nucleic acids (e.g., circulating nucleic acid, circulating tumor nucleic acid, exosomes, nucleic acids from apoptotic cells and/or necrotic cells) in body fluids, such as blood or urine (see, e.g., Siravegna et al., Nature Reviews 2017). Such tests have the advantage that they are non-invasive, can be performed without identifying suspected cancer cells through biopsy and sample nucleic acids from all parts of a cancer. However, such tests are complicated by the fact that the amount of nucleic acids released to body fluids is low and variable as is recovery of nucleic acids from such fluids in analyzable form. These sources of variation can obscure predictive value of comparing tumor mutation burden (TMB) among samples.

TMB is a measurement of the mutations carried by tumor cells in a tumor genome. TMB is a type biomarker that can be used to evaluate whether a subject diagnosed or suspected of having signs of a cancer will benefit from a cancer therapy, such as Immuno-Oncology (I-O) therapy.

SUMMARY

One aspect the disclosure relates to a method of providing a measure of tumor mutation burden in a cell-free nucleic acid test sample from a subject having a cancer type or signs of a cancer type, comprising: (a) determining a number of mutations present in cell-free nucleic acids of the test sample, and a minor allele fraction based on one or more mutations most highly represented in the cell-free nucleic acids of the test sample; and (b) normalizing the number of mutations present in the sample to a number of mutations present in control samples from other subjects with the same cancer type and a minor allele fraction within a bin of minor allele fractions including the minor allele fraction of the test sample to determine a measure of cancer mutation burden in the test sample.

In some embodiments, the number of mutations present in control samples is an average.

In some embodiments, the bin has width of no more than 20%, no more than 10% or no more than 5%.

In some embodiments, the method further comprises determining whether the number of mutations present in the sample is above a threshold, wherein the threshold is set to indicate a subject who is likely to respond positively to an immunotherapy.

In some embodiments, the normalizing comprises dividing the number of mutations in the test sample by an average number of mutations in the control samples.

In some embodiments, the normalizing comprises subtracting from the determined number of mutations in the cell-free nucleic acid test sample an average of number of mutations in the control samples within the bin.

In some embodiments, the method further comprises dividing the number of mutations in the cell-free nucleic acid test sample less the average number of mutations present in the control samples by a standard deviation of the number of mutations present in the control samples to calculate a Z-score. The average can be a mean.

In some embodiments, the normalizing comprises determining average and spread of number of mutations in at least 10, 50, 100 or 500 control samples, determining a standard score of deviation from the average in the test sample and determining whether the standard score is above a threshold number. The average can be a mean, median or mode. The spread can be represented as variance, standard deviation, or interquartile range. The standard score of deviation can be a Z-score.

In some embodiments, the normalizing further comprises dividing the determined number of mutations in the cell-free nucleic acid test sample by the average number of mutations present in the control samples in the same bin.

In some embodiments, the normalizing is implemented in a computer programmed to store values for the number of mutations present at a plurality of bins of minor allele fractions. The stored values can be a mean and standard deviation of the number of mutations present at each of the plurality of bins.

In some embodiments, comprising determining a standard score of tumor mutation burden in the subject and whether the standard score is above a threshold for control subjects consistent with responsiveness to immunotherapy.

In some embodiments, (a) comprises determining sequences of cell-free nucleic acid molecules in the test sample and comparing the resulting sequences to corresponding reference sequences to identify the number of mutations present in the sample and the minor allele fraction. The reference sequences are from hG19 or hG38.

In some embodiments, the control samples include at least 25, 50, 100, 200 or 500 control samples.

In some embodiments, at least 50,000, 100,000 or 150,000 nucleotides are sequenced in the segments of nucleic acid.

In some embodiments, (a) comprises determining presence or absence of a panel of predetermined mutations known to occur in cancer of the type present or suspected of being present in the sample, optionally wherein the mutations are somatic mutations affecting the sequence of an encoded protein.

In some embodiments, step (a) comprises linking adapters to the cell free-nucleic acids, amplifying the cell-free nucleic acids from primers binding to the adaptors and sequencing the amplified nucleic acids.

In some embodiments, the sequencing is bridge amplification sequencing, pyrosequencing, ion semiconductor sequencing, pair-end sequencing, sequencing by ligation or single molecule real time sequencing.

In one aspect, the disclosure relates to a method of treating a subject comprising: (a) determining a number of mutations present in cell-free nucleic acids of the test sample, and a minor allele fraction based on one or more mutations most highly represented in the cell-free nucleic acids of the test sample; (b) normalizing the number of mutations present in the sample to the number of mutations present in control samples from other subjects with the same cancer type and a minor allele fraction within a bin of minor allele fractions including the minor allele fraction of the test sample to determine a measure of cancer mutation burden in the test sample; and (c) administering immunotherapy to the subject if the measure of tumor mutational burden exceeds a threshold.

In some embodiments, the method is performed on a plurality of subjects to determine a measure of tumor mutation burden in each subject, wherein a greater proportion of subjects with the measure of cancer mutation burden exceeding a threshold receive immunotherapy for the cancer than subjects with the measure of tumor mutation below the threshold.

In some embodiments, all subjects in which the measure is above a first threshold receive immunotherapy and all subjects in which the measure is below a second threshold do not receive immunotherapy.

In some embodiments, the measure is a Z-score.

In some embodiments, the immunotherapy comprises administration of a checkpoint inhibitor antibody.

In some embodiments, the immunotherapy comprises administration of an antibody against PD-1, PD-2, PD-L1, PD-L2, CTLA-40, OX40, B7.1, B7He, LAG3, CD137, KIR, CCR5, CD27, or CD40.

In some embodiments, wherein the immunotherapy comprises administration of a pro-inflammatory cytokine.

In some embodiments, the immunotherapy comprises administration of T cells against the cancer type.

In some embodiments, the cancer type is a solid cancer.

In some embodiments, the cancer type is renal, mesothelioma, soft tissue, primary CNS, thyroid, liver, prostate, pancreatic, CUP, neuroendocrine, NSCLC, gastroesophageal, head and neck, SCLC, breast, melanoma, cholangiocarcinoma, gynecological, colorectal or urothelial cancer.

In some embodiments, the cancer type is a hematopoietic malignancy.

In some embodiments, the cancer type is a leukemia or lymphoma.

In one aspect, the disclosure relates to a method of treating a subject having a cancer, comprising administering an immunotherapy agent to the subject, wherein the subject has been identified for immunotherapy from a measure of cancer mutation burden of the subject determined by: (a) determining a number of mutations present in cell-free nucleic acids of sample from the subject, and a minor allele fraction for the mutation most highly represented in the cell-free nucleic acids of the test sample; and (b) normalizing the number of mutations present in the sample to the number of mutations present in control samples from other subjects with the same cancer type and a minor allele fraction within a bin of minor allele fractions including the minor allele fraction of the test sample to determine the measure of tumor mutation burden in the sample of the subject; wherein the subject is determined to have a tumor mutational burden above a threshold.

The disclosure further provides a system, comprising:

(1) a communication interface that receives, over a communication network, sequencing reads generated by sequencing cell-free nucleic acids in a test sample; and (2) a computer in communication with the communication interface, wherein the computer comprises one or more computer processors and a computer readable medium comprising machine-executable code that, upon execution by the one or more computer processors, implements a method comprising:

(a) receiving, over the communication network, the sequencing reads generated by the nucleic acid sequencer;

(b) determining a number of mutations present in the sequencing reads from the test sample, and a minor allele fraction based on one or more mutations most highly represented in sequencing reads from the test sample; and (c) normalizing the number of mutations present in the test sample to a number of mutations present in control samples from other subjects with the same cancer type and a minor allele fraction within a bin of minor allele fractions including the minor allele fraction of the test sample to determine a measure of cancer mutation burden in the test sample.

In some embodiments, the nucleic acid sequencer sequences a sequencing library generated from cell-free DNA molecules derived from a subject, wherein the sequencing library comprises the cell-free DNA molecules and adapters comprising barcodes. In some embodiments, the nucleic acid sequencer performs sequencing-by-synthesis on the sequencing library to generate the sequencing reads. In some embodiments, the nucleic acid sequencer performs pyrosequencing, single-molecule sequencing, nanopore sequencing, semiconductor sequencing, sequencing-by-ligation or sequencing-by-hybridization on the sequencing library to generate the sequencing reads. In some embodiments, the nucleic acid sequencer uses a clonal single molecule array derived from the sequencing library to generate the sequencing reads. In some embodiments, the nucleic acid sequencer comprises a chip having an array of microwells for sequencing the sequencing library to generate the sequencing reads. In some embodiments, the computer readable medium comprises a memory, a hard drive or a computer server. In some embodiments, the communication network comprises a telecommunication network, an internet, an extranet, or an intranet. In some embodiments, the communication network includes one or more computer servers capable of distributed computing. In some embodiments, the distributed computing is cloud computing. In some methods, the computer is located on a computer server that is remotely located from the nucleic acid sequencer. In some embodiments, the sequencing library further comprises sample barcodes that differentiate a sample from one or more samples. In some embodiments, the system further comprises an electronic display in communication with the computer over a network, wherein the electronic display comprises a user interface for displaying results upon implementing (a)-(c). In some embodiments, the user interface is a graphical user interface (GUI) or web-based user interface. In some embodiments, the electronic display is in a personal computer. In some embodiments, the electronic display is in an internet enabled computer. In some embodiments, the internet enabled computer is located at a location remote from the computer.

In some embodiments, the results of the systems and methods disclosed herein are used as an input to generate a report in a paper format. For example, this report may provide an indication of the called variants and/or the variants which are deemed to be deamination errors.

The various steps of the methods disclosed herein, or the steps carried out by the systems disclosed herein, may be carried out at the same or different times, in the same or different geographical locations, e.g. countries, and/or by the same or different people.

DEFINITIONS

Figure 1:
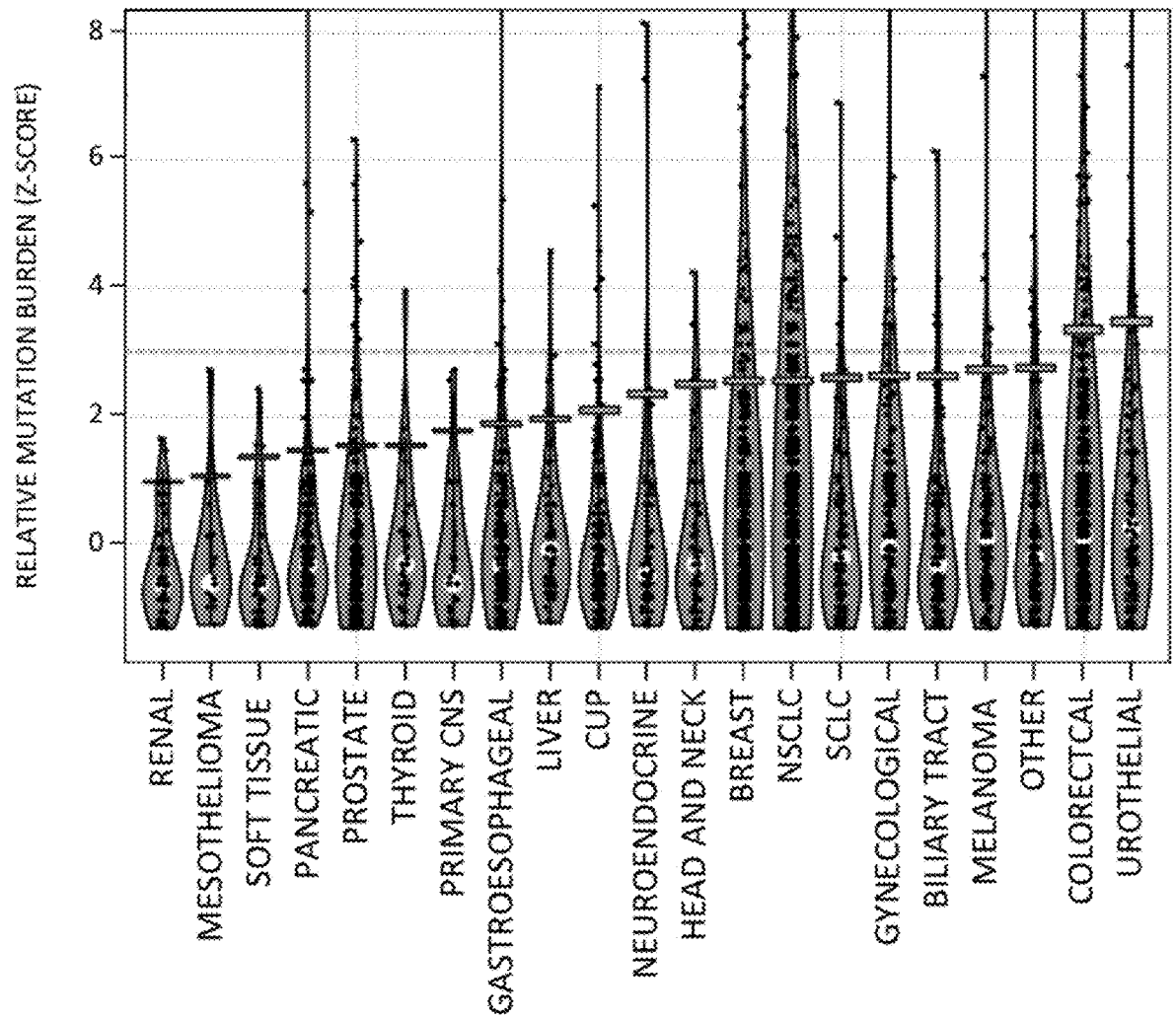
FIG. 1 depicts per-sample mutation burden distribution by tumor type. Per-sample SNV and indel count relative to other samples within clinical indication. The horizontal bars indicate the 95th percentile.

A subject refers to an animal, such as a mammalian species (preferably human) or avian (e.g., bird) species, or other organism, such as a plant. More specifically, a subject can be a vertebrate, e.g., a mammal such as a mouse, a primate, a simian or a human. Animals include farm animals, sport animals, and pets. A subject can be a healthy individual, an individual that has or is suspected of having a disease or a predisposition to the disease, or an individual that is in need of therapy or suspected of needing therapy.

For example, a subject is an individual who has been diagnosed of having a cancer, is going to receive a cancer therapy, and/or has received at least one cancer therapy. The subject can be in remission of a cancer. As another example, the subject is an individual who is diagnosed of having an autoimmune disease. As another example, the subject can be an individual who is pregnant or is planning on getting pregnant, who may have been diagnosed of or suspected of having a disease, e.g., a cancer, an auto-immune disease.

A cancer marker is a genetic variant associated with presence or risk of developing a cancer. A cancer marker can provide an indication that a subject has cancer or a higher risk of developing cancer than an age and gender matched subject of the same species that does not have the cancer marker. A cancer marker may or may not be causative of cancer.

Barcodes can be attached to one end or both ends of the nucleic acids. Barcodes can be decoded to reveal information such as the sample of origin, form or processing of a nucleic acid. Barcodes can be used to allow pooling and parallel processing of multiple samples comprising nucleic acids bearing different barcodes with the nucleic acids subsequently being deconvoluted by reading barcodes. Barcodes an also be referred to as molecular identifiers, sample identifier, tags or index tag. Barcodes can be used to distinguish samples (sample identifiers). Additionally or alternatively, barcodes can be used to distinguish different molecules in the same sample. This includes both uniquely barcoding each different molecule in the sample, or using non-uniquely barcoding each molecule. In the case of non-unique barcoding, a limited number of barcodes may be used to barcode each molecule such that different molecules can be distinguished based on their start/stop position where they map on a reference genome in combination with at least one tag. Typically then, a sufficient number of different barcodes are used such that there is a low probability (e.g. <10%, <5%, <1%, or <0.1%) that any two molecules having the same start/stop also have the same barcode. Some barcodes include multiple molecular identifiers to label samples, forms of molecule within a sample, and molecules within a form having the same start and stop points. Such barcodes can exist in the form A1i, wherein the letter indicates a sample type, the Arabic number indicates a form of molecule within a sample, and the Roman numeral indicates a molecule within a form.

Adapters are short nucleic acids (e.g., less than 500, 100 or 50 nucleotides long) usually at least partly double-stranded for linkage to either or both ends of a sample nucleic acid molecule. Adapters can include primer binding sites to permit amplification of a nucleic acid molecule flanked by adapters at both ends, and/or a sequencing primer binding site, including primer binding sites for next generation sequencing (NGS). Adapters can also include binding sites for capture probes, such as an oligonucleotide attached to a flow cell support. Adapters can also include a barcode as described above. Barcodes are preferably positioned relative to primer and sequencing primer binding sites, such that a barcode is included in amplicons and sequencing reads of a nucleic acid molecule. The same or different adapters can be linked to the respective ends of a nucleic acid molecule. Sometimes the same adapter is linked to the respective ends except that the barcode is different. A preferred adapter is a Y-shaped adapter in which one end is blunt ended or tailed as described herein, for joining to a nucleic acid molecule, which is also blunt ended or tailed with one or more complementary nucleotides. Another preferred adapter is a bell-shaped adapter, likewise with a blunt or tailed end for joining to a nucleic acid to be analyzed.

As used herein, the term "sequencing" refers to any of a number of technologies used to determine the sequence of a biomolecule, e.g., a nucleic acid such as DNA or RNA. Exemplary sequencing methods include, but are not limited to, targeted sequencing, single molecule real-time sequencing, exon sequencing, electron microscopy-based sequencing, panel sequencing, transistor-mediated sequencing, direct sequencing, random shotgun sequencing, Sanger dideoxy termination sequencing, whole-genome sequencing, sequencing by hybridization, pyrosequencing, capillary electrophoresis, gel electrophoresis, duplex sequencing, cycle sequencing, single-base extension sequencing, solid-phase sequencing, high-throughput sequencing, massively parallel signature sequencing, emulsion PCR, co-amplification at lower denaturation temperature-PCR (COLD-PCR), multiplex PCR, sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLiD™ sequencing, MS-PET sequencing, and a combination thereof. In some embodiments, sequencing can be performed by a gene analyzer such as, for example, gene analyzers commercially available from Illumina or Applied Biosystems.

The phrase "next generation sequencing" or NGS refers to sequencing technologies having increased throughput as compared to traditional Sanger- and capillary electrophoresis-based approaches, for example, with the ability to generate hundreds of thousands of relatively small sequence reads at a time. Some examples of next generation sequencing techniques include, but are not limited to, sequencing by synthesis, sequencing by ligation, and sequencing by hybridization.

The phrase "sequencing run" refers to any step or portion of a sequencing experiment performed to determine some information relating to at least one biomolecule (e.g., a nucleic acid molecule such as DNA or RNA).

DNA (deoxyribonucleic acid) is a chain of nucleotides comprising four types of nucleotides; adenine (A), thymine (T), cytosine (C), and guanine (G). RNA (ribonucleic acid) is a chain of nucleotides comprising four types of nucleotides; A, uracil (U), G, and C. Certain pairs of nucleotides specifically bind to one another in a complementary fashion (called complementary base pairing). In DNA, adenine (A) pairs with thymine (T) and cytosine (C) pairs with guanine (G). In RNA, adenine (A) pairs with uracil (U) and cytosine (C) pairs with guanine (G). When a first nucleic acid strand binds to a second nucleic acid strand made up of nucleotides that are complementary to those in the first strand, the two strands bind to form a double strand. As used herein, "nucleic acid sequencing data," "nucleic acid sequencing information," "nucleic acid sequence," "nucleotide sequence", "genomic sequence," "genetic sequence," or "fragment sequence," or "nucleic acid sequencing read" denotes any information or data that is indicative of the order of the nucleotide bases (e.g., adenine, guanine, cytosine, and thymine or uracil) in a molecule (e.g., a whole genome, whole transcriptome, exome, oligonucleotide, polynucleotide, or fragment) of a nucleic acid such as DNA or RNA. It should be understood that the present teachings contemplate sequence information obtained using all available varieties of techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, and electronic signature-based systems.

A "polynucleotide", "nucleic acid", "nucleic acid molecule", or "oligonucleotide" refers to a linear polymer of nucleosides (including deoxyribonucleosides, ribonucleosides, or analogs thereof) joined by internucleosidic linkages. Typically, a polynucleotide comprises at least three nucleosides. Oligonucleotides often range in size from a few monomeric units, e.g. 3-4, to hundreds of monomeric units. Whenever a polynucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. The letters A, C, G, and T may be used to refer to the bases themselves, to nucleosides, or to nucleotides comprising the bases, as is standard in the art.

A reference sequence is a known sequence used for purposes of comparison with experimentally determined sequences. For example, a known sequence can be an entire genome, a chromosome, or any segment thereof. A reference typically includes at least 20, 50, 100, 200, 250, 300, 350, 400, 450, 500, 1000, or more nucleotides. A reference sequence can align with a single contiguous sequence of a genome or chromosome or can include non-contiguous segments aligning with different regions of a genome or chromosome. Reference human genomes include, e.g., hG19 and hG38.

A first single stranded nucleic acid sequence overlaps with a second single stranded sequence if the first nucleic acid sequence or its complement and the second nucleic acid sequence or its complement align with overlapping but non-identical segments of a contiguous reference sequence, such as the sequence of a human chromosome. A fully or partially double stranded nucleic acid overlaps with another fully or partially double stranded nucleic acid if either of its strands overlaps those of the other nucleic acid.

"Average" refers to any statistical measure of central tendency including, without limitation, mean, median, mode.

"Spread" refers to any statistical measure of dispersion, including, without limitation, variance, standard deviation and interquartile range.

"Standard score" refers to any statistical measure of distance from an average, including, without limitation, a normalized score or a Z-score (number of standard deviation from average).

Normalized tumor mutation burden refers to a standard score of tumor burden compared with control subjects. It includes measure of the tumor mutation burden in a test nucleic acid molecule sample adjusted to account for random variations between samples in factors affecting detection of such mutations, such as release of nucleic acids from cancer cells to a body fluid, and recovery of nucleic acids from the body fluid in analyzable form.

A mutation refers to a variation from a known reference sequence and includes mutations such as for example, SNVs, copy number variations/aberrations, indels and gene fusions. A mutation can be a germline or somatic mutation. A preferred reference sequence for purposes of comparison is a wildtype genomic sequence of the species of the subject providing a test sample, typically the human genome.

A variant can be referred to as an allele. A variant is usually presented at a frequency of 50% (0.5) or 100% (1), depending on whether the allele is heterozygous or homozygous. For example, germline variants are inherited and usually have a frequency of 0.5 or 1. Somatic variants; however, are acquired variants and usually have a frequency of <0.5.

Major and minor alleles of a genetic locus refer to nucleic acids harboring the locus in which the locus is occupied by a nucleotide of a reference sequence, and a variant nucleotide different than the reference sequence respectively. Measurements at a locus can take the form of allelic fractions (AFs), which measure the frequency with which an allele is observed in a sample.

The terms "minor allele frequency" may refer to the frequency at which minor alleles (e.g., not the most common allele) occurs in a given population of nucleic acids, such as a sample. Genetic variants at a low minor allele frequency may have a relatively low frequency of presence in a sample.

A "minor allele fraction (MAF)" refers to the fraction of DNA molecules harboring an allelic alteration (e.g., a mutation) at a given genomic position in a given sample. A MAF of a somatic variant can be less than 0.5, 0.1, 0.05, or 0.01 of all somatic variants or alleles present at a given locus. For example, a MAF of a somatic variant is <0.05. Minor allele fraction may also be used interchangeably with "mutant allele fraction."

The terms "neoplasm" and "tumor" are used interchangeably. They referred to abnormal growth of cells in a subject. A neoplasm or tumor can be benign, potentially malignant, or malignant. A malignant tumor is a referred to as a cancer or a cancerous tumor.

The terms "tumor mutation burden (TMB)", "tumor mutational burden (TMB)", or "cancer mutation burden" are used interchangeably. They refer to the total number of mutations, e.g., somatic mutations, present in a sequenced portion of a tumor genome. TMB can refer to the number of coding, base substitution, and indel mutations per megabase of a tumor genome being examined. They can be indicative for detecting, evaluating, calculating, or predicting the sensitivity and/or resistance to a cancer therapeutic agent or drug, e.g., immune checkpoint inhibitors, antibodies. Tumors that have higher levels of TMB may express more neoantigens, a type of cancer-specific antigen, may allow for a more robust immune response and therefore a more durable response to immunotherapy. The immune system relies on a sufficient number of neoantigens in order to appropriately respond, the number of somatic mutations may be acting as a proxy for determining the number of neoantigens in a tumor. TMB may be used to deduce robustness of an immune response to a drug treatment and efficacy of a drug treatment in a subject. Germline and somatic variants can be bioinformatically distinguished to identify antigenic somatic variants, such as described in PCT/US2018/52087, incorporated by reference herein.

A threshold is a predetermined value used to characterize experimentally determined values of the same parameter for different samples depending on their relation to the threshold.

The terms "processing", "calculating", and "comparing" can be used interchangeably. The term can refer to determining a difference, e.g., a difference in number or sequence. For example, gene expression, copy number variation (CNV), indel, and/or single nucleotide variant (SNV) values or sequences can be processed.

"Cancer type" refers to type or subtype defined, e.g., by histopathology. Cancer type can be defined by any conventional criterion, such as cancer of the same tissue (e.g., blood cancers, CNS, brain cancers, lung cancers (small cell and non-small cell), skin cancers, nose cancers, throat cancers, liver cancers, bone cancers, lymphomas, pancreatic cancers, bowel cancers, rectal cancers, thyroid cancers, bladder cancers, kidney cancers, mouth cancers, stomach cancers, breast cancers, prostate cancers, ovarian cancers, lung cancers, intestine cancers, soft tissue cancers, thyroid cancers, neuroendocrine cancers, gastroesophageal cancers, head and neck cancers, gynecological cancers, colorectal cancers, urothelial cancers, solid state cancers, heterogeneous cancers, homogenous cancers), unknown primary origin and the like, and/or of the same cell lineage (e.g., carcinoma, sarcoma, lymphoma, cholangiocarcinoma, leukemia, mesothelioma, melanoma, or glioblastoma) and/or cancer markers, such as Her2, CA15-3, CA19-9, CA-125, CEA, AFP, PSA, HCG, hormone receptor and NMP-22. Cancers can also be classified by stage (e.g., stage 1, 2, 3, or 4) and whether of primary or secondary origin.

DETAILED DESCRIPTION

I. General

The disclosure is premised in part on the result that values for tumor mutation burden from different samples can be made more comparable to each other or control standards by a normalization regime that takes into account the minor allele fraction of highly rated mutations in a sample. Such analysis can provide an indication where the tumor mutation burden of a test sample lies on a distribution of tumor mutation burdens in a control population, and thus, whether the individual providing the test sample is likely to be amenable to immunotherapy to treat a cancer.

II. Determining Tumor Mutation Burden and Normalizing

Nucleic acids present in a sample can be processed and sequenced as further described below. Sequencing reveals a total number of mutations present and detected in a sample, i.e., a total number of loci at which a minor allele is detected preferably at sufficient frequency in different nucleic acid molecules in the sample as to be statistically unlikely to represent a sequencing artifact (e.g., $p \leq 0.05$). The total number of mutations determined can represent mutations present anywhere in the genome of the individual providing the sample, or any fraction thereof, such as a particular chromosome, or a set of non-contiguous genomic segments, such as a set of such segments known to harbor loci at which mutations associated with cancer occur. The mutations determined can be exclusively mutations causing changes in the sequence of an encoded protein, e.g., SNV, indel, fusion, or can include any types of mutations that do not cause changes in the sequence of an encoded protein, e.g., copy number variations, copy number aberrations. If any types of mutations are determined, mutations that change amino acid sequences of encoded proteins can be selected out before subsequent processing. The mutations can include germline mutations, somatic mutations, or both.

Although mutations encoding amino acid changes in encoded proteins are likely better correlated with amenability to immunotherapy than other mutations, sampling all mutations may correlate better with the number of mutations that changes sequence in encoded protein sequences, than counting such mutations directly due to loss of some such mutations below a level of detection. Thus, both approaches have advantages and can be used.

Sequencing also provides the minor allele fraction of any or all mutations detected (or subset thereof selected for subsequent processing). The minor allele fraction means the proportion of all sequenced nucleic acids in a sample including a locus of mutation harboring a minor allele (as distinct from a wildtype allele). Thus, the minor allele fraction can be represented by a number between 0 and 1. If more than one minor allele can occur at a locus, the minor allele fraction can be defined as the fraction of any of the minor alleles or the aggregate fraction of all or any subset of the minor alleles.

The minor allele fraction of the highest represented mutant or an average minor allele fraction of a set of highly represented mutants is used in the subsequent normalization. If a set of highly represented mutants is used the set can represent for example, the top 2, 3, 5 or 10 most highly represented mutants.

The analysis described for a test sample can also be carried out on a population of control samples to provide a dataset for comparison. The control population can include samples from e.g., at least 10, 20, 25, 50, 100, 200, 250 500, 1,000, 5,000, 10,000, 50,000 or more individuals. The control samples can be samples from subjects with the same cancer type as a test sample. Each control sample is likewise analyzed for total tumor mutation burden and minor allele fraction of the highest represented mutation or set of mutations. Preferably, minor allele fraction is determined in the same way between test samples and control samples (i.e., based on the highest represented mutation or same set of highly represented mutations). Such is also the case for the counting of mutations. For example, if mutations occurring anywhere in the genome are counted in the test sample, the same is preferably the case in the control samples. Likewise, if only mutations affecting an encoded protein sequence are counted for a test sample, the same is the case for control samples.

The control samples can then be sorted into bins by the determined minor allele fractions. The bins can be of equal size (e.g., 0.05-0.1, 0.1-0.15, 0.15-0.2, 0.2-0.25) or the bins can vary in sizes, for example, to make uniform the number of control samples fitting in each bin. The bins can also be defined as a percentage of the total variation in minor allele fraction. For example, if the minor allele fraction of the most highly represented mutation or mutations in the control population varies between 0.1 and 0.5, the bins can be defined by a percentage of that range (e.g., 5%, 10% or 20% per bin). An average tumor mutation burden is then determined for the control samples in each bin. For example, if there are three control samples with mutation burdens of 3, 4, and 5 in a bin of 0.1-0.15 then the average cancer mutation burden for that bin is 4. A standard deviation can also be calculated for the cancer mutation values within a bin. Such a collection of bins can populate a data for comparison with test samples of the same cancer type. The bin may have width of no more than 20%, no more than 10%, or no more than 5%.

The control population only needs to be analyzed once and the resulting data can serve for comparison with any number of test samples. However, the control population can also be supplemented with data from additional individuals with the same cancer type.

The same type of analysis can also be performed on additional control populations with other types of cancer for comparison with test samples with these other forms of cancer.

The number of tumor mutations measured in a test sample can then be compared with the average number of mutations of a bin of control samples defined by a range of minor allele frequencies that includes that of the test sample. For example, if the test sample has a minor allele frequency of the most highly represented minor allele of 0.125, then a bin including minor allele frequencies from 0.1 to 0.15 can be chosen for comparison. A simple numerical comparison (e.g., subtracting the average tumor mutation burden of the control samples from that of the test sample, or dividing the tumor mutation burden of the test sample by the average value of the control samples) indicates whether the tumor mutation burden of a sample is at, above or below average. For example, if the tumor mutation burden of a test sample is 5 and the average of the minor allele matched representation bin is 3, then the tumor mutation burden of the test sample can be represented as 2 mutations more than average or 5/3=167% of average.

However, a more quantitative comparison can be performed by calculating a Z-score. A Z-score is calculated by subtracting from the test sample tumor mutation burden the average tumor mutation burden of the matched bin and dividing the result by the standard deviation of the variation in tumor mutation within the bin. The Z-score can be positive (higher than average mutation burden), negative (lower than average cancer mutation burden) or zero (average mutation burden). The magnitude of the Z-score (positive or negative) is an indication of the extent to which a test sample is above or below average in tumor mutation burden.

A normalized tumor mutation burden of a test sample from a subject (as represented by e.g., a Z-score) from a subject provides an indication of the amenability of the subject to immunotherapy. In general, the higher the normalized tumor mutation burden (as can be represented by a higher positive Z-score), the more amenable the subject is to immunotherapy. Without being bound to any theory, the more mutations indicates presence of more neoepitopes forming non-self targets for immunotherapy. Conversely, a lower normalized mutation represented by e.g., a negative Z-score, the less amenable a subject is to immunotherapy.

One or more thresholds of normalized tumor mutation burden can be set to determine or at least provide an indication (which can be used in combination with other factors) to determine whether a subject receives or continues to receive, or discontinue receiving an immunotherapy. For example, a threshold can be set so that subjects at or above the threshold receive or continue to receive immunotherapy, and subjects below the threshold do not receive or discontinue receiving immunotherapy. Alternatively, two thresholds can be set with subjects at or above the higher threshold receiving or continuing to receive immunotherapy and subjects at or below the lower threshold not receiving or discontinuing receipt of immunotherapy. Subjects between the thresholds can be evaluated by additional factors as to whether they should receive or continue to receive immunotherapy.

Thresholds can be determined empirically by observing responses to immunotherapy in subjects characterized for normalized tumor mutation burden to determine thresholds best correlated with a beneficial response or lack thereof to immunotherapy. Thresholds can alternatively set at predefined points on a scale, such as for example, subjects with a positive Z-score receiving or continuing to receive therapy, and/or subjects with a negative Z-score not receiving or discontinuing receipt of immunotherapy. As another example, subjects with a Z-score above 1, 2, or 3 can receive or continue to receive therapy. As another example, subjects with a Z-score above less than 1 can discontinue to receive therapy. As another example, subjects with a positive Z score placing the subject with a Z-score representing e.g., at least the highest 75%, 50%, 25%, 15%, 10%, or 5% of Z-scores of subjects with that type of cancer can receive or continuing to receive immunotherapy with other subjects not receiving immunotherapy.

As mentioned, normalized tumor mutation burden can be used with or without other factors in determining whether immunotherapy is administered or continued to be administered. Such other facts can include condition of the subject, response of the subject to other therapies previously tried, and availability of other therapies not yet tried on the subject, among other factors. Thus, not necessarily every subject over a threshold receives or continues to receive immunotherapy or under a threshold does not, but in general a higher proportion of subjects with a normalized tumor mutation burden over a threshold receive or continue to receive immunotherapy than is the case for subjects with a normalized tumor mutation burden below a threshold.

III. Immunotherapy

Immunotherapy refers to treatment with one or more agents that act to stimulate the immune system so as to kill or at least to inhibit growth of cells of a cancer, and preferably to reduce further growth of the cancer, reduce the size of the cancer and/or eliminate the cancer. Some such agents bind to a target present on cells of the cancer; some bind to a target present on immune cells and not on the cancer; some bind to a target present on both cells of the cancer and immune cells. Such agents include, but are not limited to, checkpoint inhibitors and/or antibodies. Checkpoint inhibitors are inhibitors of pathways of the immune system that maintain self-tolerance and modulate the duration and amplitude of physiological immune responses in peripheral tissues to minimize collateral tissue damage (see, e.g., Pardoll, Nature Reviews Cancer 12, 252-264 (2012)). Exemplary agents include antibodies against any of PD-1, PD-2, PD-L1, PD-L2, CTLA-40, OX40, B7.1, B7He, LAG3, CD137, KIR, CCR5, CD27, or CD40. Other exemplary agents include proinflammatory cytokines, such as IL-1β, IL-6, and TNF-α. Other exemplary agents are T-cells activated against a tumor, such as by expressing of a chimeric antigen targeting a tumor antigen from the T-cell. In some embodiments, immunotherapy stimulates the immune system to attack tumor antigens distinguished from wildtype counterparts by the presence of mutation(s).

IV. Other Applications

Normalized tumor mutation burdens determined by the present methods can be used to diagnose presence of conditions, particularly cancer, in a subject, to characterize conditions (e.g., staging cancer or determining heterogeneity of a cancer), monitor response to treatment of a condition, effect prognosis risk of developing a condition or subsequent course of a condition. Normalized tumor mutation burdens can also be used for characterizing a specific form of cancer. Cancers are often heterogeneous in both composition and staging. Genetic profile data may allow characterization of specific sub-types of cancer that may be important in the diagnosis or treatment of that specific sub-type. This information may also provide a subject or practitioner clues regarding the prognosis of a specific type of cancer and allow either a subject or practitioner to adapt treatment options in accord with the progress of the disease. Some cancers progress, becoming more aggressive and genetically unstable. Other cancers may remain benign, inactive or dormant. Normalized tumor mutation burden can be useful in determining disease progression.

Normalized tumor mutation burdens can also be used in selecting treatments beyond immunotherapy and in determining the efficacy of a particular treatment option. Successful treatment options may initially increase normalized tumor mutation burden if the treatment is successful as more cancers may die and shed nucleic acids followed by a decrease as the cancer shrinks or dies. Successful treatment may also decrease tumor mutation burden and/or minor allele fraction without an initial increase. Additionally, if a cancer is observed to be in remission after treatment, normalized tumor mutation burden can be used to monitor residual disease or recurrence of disease as indicated by a normalized mutation count in a body fluid.

V. Computer Implementation

The present methods can be computer-implemented, such that any or all of the steps described in the specification or appended claims other than wet chemistry steps can be performed in a suitable programmed computer. The computer can be a mainframe, personal computer, tablet, smart phone, cloud, online data storage, remote data storage, or the like. The computer can be operated in one or more locations.

A computer program for analyzing a nucleic acid population can include codes for performing any of the steps other than wet chemistry steps described in the specification or in the appended claims; for example, code for receiving raw sequencing data, code for determining sequences of nucleic acids from such data, codes for determining a number of mutations present in the determined sequences, code for categorizing mutations as affecting the sequence of an encoded protein or otherwise, code for determine the minor allele fraction of any of the mutations, and code for comparing the number of mutations present in a sample to the number mutations present in control samples from other subjects with the same cancer type and a minor allele fraction within a bin of minor allele fractions including the minor allele fraction of the test sample to determine a measure of cancer mutation burden in the test sample, and code for outputting a normalized mutation burden optionally with an associated immunotherapy treatment.

The present methods can be implemented in a system (e.g., a data processing system) for analyzing a nucleic acid population. The system can also include a processor, a system bus, a main memory and optionally an auxiliary memory coupled to one another to perform one or more of the steps described in the specification or appended claims, such as the following: receiving raw sequencing data, determining sequences of nucleic acids from such data, identifying mutations within the determined sequences, categorizing the mutations as affecting an encoded protein sequence or otherwise, determining minor allele fraction for any determined mutation and comparing the number of mutations present in the sample to the number of mutations present in control samples from other subjects with the same cancer type and a minor allele fraction within a bin of minor allele fractions including the minor allele fraction of the test sample to determine a measure of cancer mutation burden in the test sample, and outputting a normalized mutation burden optionally with an immunotherapy treatment. The system memory can also store control data from various populations with different cancer types. For any such population, the data can include numbers of mutations present in subjects, minor allele frequencies of some or all of such mutations, bins of minor allele frequencies characterized by average mutation frequencies standard deviations for numbers of mutations of samples falling within a bin. The system can also include a display or printer for outputting results, such as cancer mutation burden of a sample expressed e.g., as a Z-score, and and/or a recommended future treatment, such as administering immunotherapy or continuing immunotherapy. The system can also include a keyboard and/or pointer for providing user input, such as defining cancer types, set of mutations on which the analysis is to be performed or setting thresholds, among other accessories. The system can also include a sequencing apparatus coupled to the memory to provide raw sequencing data.

Various steps of the present methods can utilize information and/or programs and generate results that are stored on computer-readable media (e.g., hard drive, auxiliary memory, external memory, server; database, portable memory device (e.g., CD-R, DVD, ZIP disk, flash memory cards), and the like. For example, information used for and results generated by the methods that can be stored on computer-readable media include control data from various populations with different types of cancer as described above, references sequences, raw sequencing data, sequenced nucleic acids, mutations, minor allele fractions, measures of normalized mutation burden, such as Z-scores, thresholds, and immunotherapy treatment regimes associated with normalized mutation burdens over a threshold in various cancer types.

The present disclosure also includes a kit comprising instructions for providing a measure of tumor mutation burden in a sample. The kit may include a machine-readable medium containing one or more programs which when executed implement the steps of the present methods. The kit may not include a physical machine-readable medium, but rather access to the cloud or an online data storage that provides a platform through which a user may perform analysis of tumor mutation burden in the sample.

The disclosure can be implemented in hardware and/or software. For example, different aspects of the disclosure can be implemented in either client-side logic or server-side logic. The disclosure or components thereof can be embodied in a fixed media program component containing logic instructions and/or data that when loaded into an appropriately configured computing device cause that device to perform according to the disclosure. A fixed media containing logic instructions can be delivered to a viewer on a fixed media for physically loading into a viewer's computer or a fixed media containing logic instructions may reside on a remote server that a viewer accesses through a communication medium to download a program component.

Figure 2:
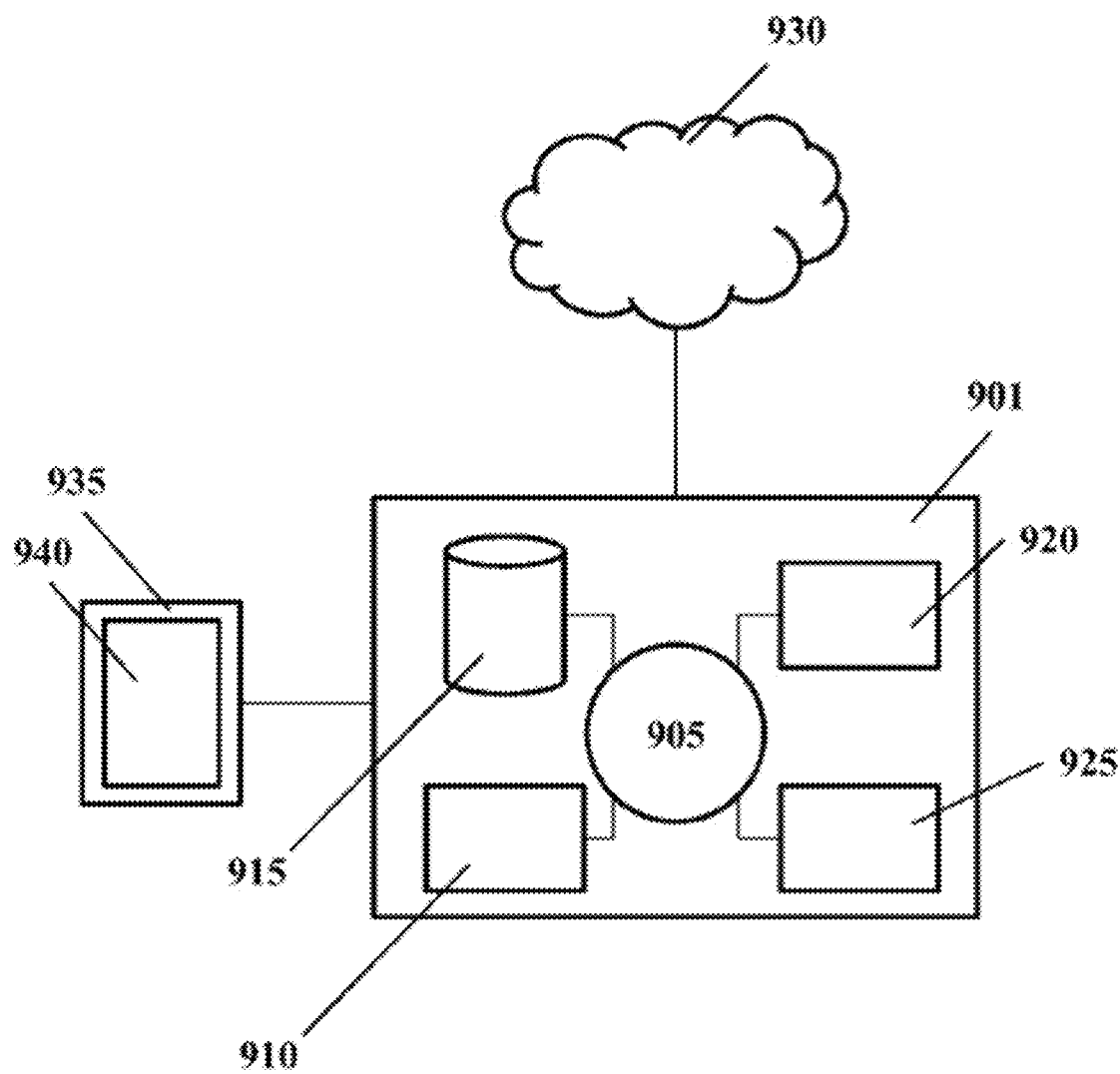
FIG. 2 shows a computer system for implementing the disclosed methods.

The present disclosure provides computer control systems that are programmed to implement methods of the disclosure. FIG. 2 shows a computer system 901 that is programmed or otherwise configured to implement methods of the present disclosure. The computer system 901 includes a central processing unit (CPU, also "processor" and "computer processor" herein) 905, which can be a single core or multi core processor, or a plurality of processors for parallel processing. The computer system 901 also includes memory or memory location 910 (e.g., random-access memory, read-only memory, flash memory), electronic storage unit 915 (e.g., hard disk), communication interface 920 (e.g., network adapter) for communicating with one or more other systems, and peripheral devices 925, such as cache, other memory, data storage and/or electronic display adapters. The memory 910, storage unit 915, interface 920 and peripheral devices 925 are in communication with the CPU 905

Through a communication bus (solid lines), such as a motherboard. The storage unit 915 can be a data storage unit (or data repository) for storing data. The computer system 901 can be operatively coupled to a computer network ("network") 930 with the aid of the communication interface 920. The network 930 can be the Internet, an internet and/or extranet, or an intranet and/or extranet that is in communication with the Internet. The network 930 in some cases is a telecommunication and/or data network. The network 930 can include a local area network. The network 930 can include one or more computer servers, which can enable distributed computing, such as cloud computing. The network 930, in some cases with the aid of the computer system 901, can implement a peer-to-peer network, which may enable devices coupled to the computer system 901 to behave as a client or a server.

The CPU 905 can execute a sequence of machine-readable instructions, which can be embodied in a program or software. The instructions may be stored in a memory location, such as the memory 910. The instructions can be directed to the CPU 905, which can subsequently program or otherwise configure the CPU 905 to implement methods of the present disclosure. Examples of operations performed by the CPU 905 can include fetch, decode, execute, and writeback.

The CPU 905 can be part of a circuit, such as an integrated circuit. One or more other components of the system 901 can be included in the circuit. In some cases, the circuit is an application specific integrated circuit (ASIC).

The storage unit 915 can store files, such as drivers, libraries and saved programs. The storage unit 915 can store user data, e.g., user preferences and user programs. The computer system 901 in some cases can include one or more additional data storage units that are external to the computer system 901, such as located on a remote server that is in communication with the computer system 901 through an intranet or the Internet.

The computer system 901 can communicate with one or more remote computer systems through the network 930. For instance, the computer system 901 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 901 via the network 930.

Methods as described herein can be implemented by way of machine (e.g., computer processor) executable code stored on an electronic storage location of the computer system 901, such as, for example, on the memory 910 or electronic storage unit 915. The machine executable or machine readable code can be provided in the form of software. During use, the code can be executed by the processor 905. In some cases, the code can be retrieved from the storage unit 915 and stored on the memory 910 for ready access by the processor 905. In some situations, the electronic storage unit 915 can be precluded, and machine-executable instructions are stored on memory 910.

The code can be pre-compiled and configured for use with a machine having a processor adapted to execute the code, or can be compiled during runtime. The code can be supplied in a programming language that can be selected to enable the code to execute in a precompiled or as-compiled fashion.

Aspects of the systems and methods provided herein, such as the computer system 901, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk.

"Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "Storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 901 can include or be in communication with an electronic display 935 that comprises a user interface (UI) 940 for providing, for example, a report. Examples of LA's include, without limitation, a graphical user interface (GUI) and web-based user interface.

Methods and systems of the present disclosure can be implemented by way of one or more algorithms. An algorithm can be implemented by way of software upon execution by the central processing unit 905.

VI. General Features of the Methods

1. Samples

A sample can be any biological sample isolated from a subject. Samples can include body tissues, such as known or suspected solid tumors, whole blood, platelets, serum, plasma, stool, red blood cells, white blood cells or leucocytes, endothelial cells, tissue biopsies, cerebrospinal fluid synovial fluid, lymphatic fluid, ascites fluid, interstitial or extracellular fluid, the fluid in spaces between cells, including gingival crevicular fluid, bone marrow, pleural effusions, cerebrospinal fluid, saliva, mucous, sputum, semen, sweat, urine. Samples are preferably body fluids, particularly blood and fractions thereof such as plasma and serum, and urine. Such samples include nucleic acids shed from tumors. The nucleic acids can include DNA and RNA and can be in double and/or single-stranded forms. A sample can be in the form originally isolated from a subject or can have been subjected to further processing to remove or add components, such as cells, enrich for one component relative to another, or convert one form of nucleic acid to another, such as RNA to DNA or single-stranded nucleic acids to double-stranded. Thus, for example, a body fluid for analysis is plasma or serum containing cell-free nucleic acids, e.g., cell-free DNA (cfDNA).

The volume of body fluid can depend on the desired read depth for sequenced regions. Exemplary volumes are 0.4-40 ml, 5-20 ml, 10-20 ml. For example, the volume can be 0.5 ml, 1 ml, 5 ml 10 ml, 20 ml, 30 ml, or 40 ml. A volume of sampled plasma may be 5 to 20 ml.

The sample can comprise various amount of nucleic acid that contains genome equivalents. For example, a sample of about 30 ng DNA can contain about 10,000 ($10^4$) haploid human genome equivalents and, in the case of cfDNA, about 200 billion ($2\times10^4$) individual polynucleotide molecules. Similarly, a sample of about 100 ng of DNA can contain about 30,000 haploid human genome equivalents and, in the case of cfDNA, about 600 billion individual molecules.

A sample can comprise nucleic acids from different sources, e.g., from cells and cell free. A sample can comprise nucleic acids carrying mutations. For example, a sample can comprise DNA carrying germline mutations and/or somatic mutations. A sample can comprise DNA carrying cancer-associated mutations (e.g., cancer-associated somatic mutations).

Exemplary amounts of cell-free nucleic acids in a sample before amplification range from about 1 fg to about 1 µg, e.g., 1 pg to 200 ng, 1 ng to 100 ng, 10 ng to 1000 ng. For example, the amount can be up to about 600 ng, up to about 500 ng, up to about 400 ng, up to about 300 ng, up to about 200 ng, up to about 100 ng, up to about 50 ng, or up to about 20 ng of cell-free nucleic acid molecules. The amount can be at least 1 fg, at least 10 fg, at least 100 fg, at least 1 pg, at least 10 pg, at least 100 pg, at least 1 ng, at least 10 ng, at least 100 ng, at least 150 ng, or at least 200 ng of cell-free nucleic acid molecules. The amount can be up to 1 femtogram (fg), 10 fg, 100 fg, 1 picogram (pg), 10 pg, 100 pg, 1 ng, 10 ng, 100 ng, 150 ng, or 200 ng of cell-free nucleic acid molecules. The method can comprise obtaining 1 femtogram (fg) to 200 ng.

A cell-free nucleic acid sample refers to a sample containing cell-free nucleic acids. Cell-free nucleic acids are nucleic acids not contained within or otherwise bound to a cell or in other words nucleic acids remaining in a sample of removing intact cells. Cell-free nucleic acids can be referred to all non-encapsulated nucleic acid sourced from a bodily fluid (e.g., blood, urine, CSF, etc.) from a subject. Cell-free nucleic acids include DNA (cfDNA), RNA (cfRNA), and hybrids thereof, including genomic DNA, mitochondrial DNA, circulating DNA, siRNA, miRNA, circulating RNA (cRNA), tRNA, rRNA, small nucleolar RNA (snoRNA), Piwi-interacting RNA (piRNA), long non-coding RNA (long ncRNA), or fragments of any of these. Cell-free nucleic acids can be double-stranded, single-stranded, or a hybrid thereof. A cell-free nucleic acid can be released into bodily fluid through secretion or cell death processes, e.g., cellular necrosis and apoptosis. Some cell-free nucleic acids are released into bodily fluid from cancer cells e.g., circulating tumor DNA (ctDNA). Others are released from healthy cells. ctDNA can be non-encapsulated tumor-derived fragmented DNA. Cell-free fetal DNA (cffDNA) is fetal DNA circulating freely in the maternal blood stream.

A cell-free nucleic acid or proteins associated with it can have one or more epigenetic modifications, for example, a cell-free nucleic acid can be acetylated, 5-methylated, ubiquitylated, phosphorylated, sumoylated, ribosylated, and/or citrullinated.

Cell-free nucleic acids have an exemplary size distribution of about 100-500 nucleotides, with molecules of 110 to about 230 nucleotides representing about 90% of molecules, with a mode of about 168 nucleotides in humans and a second minor peak in a range between 240 to 440 nucleotides. Cell-free nucleic acids can be about 160 to about 180 nucleotides, or about 320 to about 360 nucleotides, or about 440 to about 480 nucleotides.

Cell-free nucleic acids can be isolated from bodily fluids through a partitioning step in which cell-free nucleic acids, as found in solution, are separated from intact cells and other non-soluble components of the bodily fluid. Partitioning may include techniques such as centrifugation or filtration. Alternatively, cells in bodily fluids can be lysed and cell-free and cellular nucleic acids processed together. Generally, after addition of buffers and wash steps, cell-free nucleic acids can be precipitated with an alcohol. Further clean up steps may be used such as silica based columns to remove contaminants or salts. Non-specific bulk carrier nucleic acids, for example, may be added throughout the reaction to optimize certain aspects of the procedure such as yield.

After such processing, samples can include various forms of nucleic acids including double-stranded DNA, single-stranded DNA and/or single-stranded RNA. Optionally, single stranded DNA and/or single stranded RNA can be converted to double stranded forms so they are included in subsequent processing and analysis steps.

2. Amplification

Sample nucleic acids flanked by adapters can be amplified by PCR and other amplification methods typically primed from primers binding to primer binding sites in adapters flanking a DNA molecule to be amplified. Amplification methods can involve cycles of extension, denaturation and annealing resulting from thermocycling or can be isothermal as in transcription mediated amplification. Other amplification methods include the ligase chain reaction, strand displacement amplification, nucleic acid sequence based amplification, and self-sustained sequence based replication.

One or more amplifications can be applied to introduce barcodes to a nucleic acid molecule using conventional nucleic acid amplification methods. The amplification can be conducted in one or more reaction mixtures. Barcodes can be introduced simultaneously, or in any sequential order. Barcodes can be introduced prior to and/or after sequence capturing. In some cases, only barcodes to label individual nucleic acid molecules are introduced prior to probe capturing while barcodes to label samples are introduced after sequence capturing. In some cases, both the barcodes to label individual nucleic acids and barcodes to label samples are introduced prior to probe capturing. In some cases, the barcodes to label samples are introduced after sequence capturing. Usually, sequence capturing involves introducing a single-stranded nucleic acid molecule complementary to a targeted sequence, e.g., a coding sequence of a genomic region and mutation of such region is associated with a cancer type. Typically, the amplifications generate a plurality of non-uniquely or uniquely barcoded nucleic acid amplicons with barcodes labelling individual nucleic acids and/or samples at a size ranging from 200 nt to 700 nt, 250 nt to 350 nt, or 320 nt to 550 nt. In some embodiments, the amplicons have a size of about 300 nt. In some embodiments, the amplicons have a size of about 500 nt.

3. Barcode

Barcodes can be incorporated into or otherwise joined to adapters by chemical synthesis, ligation, overlap extension PCR among other methods. Generally, assignment of unique or non-unique barcodes in reactions follows methods and systems described by US patent applications 20010053519, 20110160078, and U.S. Pat. Nos. 6,582,908 and 7,537,898 and 9,598,731.

Barcodes can be linked to sample nucleic acids randomly or non-randomly. In some cases, they are introduced at an expected ratio of barcodes (e.g., a combination of unique or non-unique barcodes) to microwells. For example, the barcodes may be loaded so that more than about 1, 2, 3, 4, 5, 6, 7, 8, 9, 10, 20, 50, 100, 500, 1000, 5000, 10000, 50,000, 100,000, 500,000, 1,000,000, 10,000,000, 50,000,000 or 1,000,000,000 barcodes are loaded per genome sample. In some cases, the barcodes may be loaded so that less than about 2, 3, 4, 5, 6, 7, 8, 9, 10, 20, 50, 100, 500, 1000, 5000, 10000, 50,000, 100,000, 500,000, 1,000,000, 10,000,000, 50,000,000 or 1,000,000,000 barcodes are loaded per genome sample. In some cases, the average number of barcodes loaded per sample genome is less than, or greater than, about 1, 2, 3, 4, 5, 6, 7, 8, 9, 10, 20, 50, 100, 500, 1000, 5000, 10000, 50,000, 100,000, 500,000, 1,000,000, 10,000, 000, 50,000,000 or 1,000,000,000 barcodes per genome sample. The barcodes can be unique or non-unique.

A preferred format uses 20-50 different barcodes, ligated to both ends of a target molecule creating 20-50×20-50 tags, e.g., 400-2500 barcodes. Such numbers of barcodes are sufficient that different molecules having the same start and stop points have a high probability (e.g., at least 94%, 99.5%, 99.99%, 99.999%) of receiving different combinations of tags.

In some cases, barcodes may be predetermined or random or semi-random sequence oligonucleotides. In other cases, a plurality of barcodes may be used such that barcodes are not necessarily unique to one another in the plurality. In this example, barcodes may be attached (e.g., by ligation or PCR amplification) to individual molecules such that the combination of the barcode and the sequence it may be attached to creates a unique sequence that may be individually tracked. As described herein, detection of non-unique barcodes in combination with sequence data of beginning (start) and end (stop) portions of sequence reads may allow assignment of a unique identity to a particular molecule. The length, or number of base pairs, of an individual sequence read may also be used to assign a unique identity to such a molecule. As described herein, fragments from a single strand of nucleic acid having been assigned a unique identity, may thereby permit subsequent identification of fragments from the parent strand, and/or a complementary strand.

4. Sequencing

Sample nucleic acids, optionally flanked by adapters, with or without prior amplification can be subject to sequencing. Sequencing methods include, for example, Sanger sequencing, high-throughput sequencing, pyrosequencing, sequencing-by-synthesis, single-molecule sequencing, nanopore sequencing, semiconductor sequencing, sequencing-by-ligation, sequencing-by-hybridization, RNA-Seq (Illumina), Digital Gene Expression (Helicon), Next generation sequencing (NGS), Single Molecule Sequencing by Synthesis (SMSS) (Helicon), massively-parallel sequencing, Clonal Single Molecule Array (Solexa), shotgun sequencing, Ion Torrent, Oxford Nanopore, Roche Genia, Maxim-Gilbert sequencing, primer walking, sequencing using PacBio, SOLiD, Ion Torrent, or Nanopore platforms. Sequencing reactions can be performed in a variety of sample processing units, which may be multiple lanes, multiple channels, multiple wells, or other means of processing multiple sample sets substantially simultaneously. Sample processing unit can also include multiple sample chambers to enable processing of multiple runs simultaneously.

The sequencing reactions can be performed on one or more fragments types known to contain markers of cancer of other disease. The sequencing reactions can also be performed on any nucleic acid fragments present in the sample. The sequence reactions may provide for sequence coverage of the genome of at least 5%, 10%, 15%, 20%, 25%, 30%, 40%, 50%, 60%, 70%, 80%, 90%, 95%, 99%, 99.9% or 100%. In other cases, sequence coverage of the genome may be less than 5%, 10%, 15%, 20%, 25%, 30%, 40%, 50%, 60%, 70%, 80%, 90%, 95%, 99%, 99.9% or 100%.

Simultaneous sequencing reactions may be performed using multiplex sequencing. In some cases, cell free polynucleotides may be sequenced with at least 1000, 2000, 3000, 4000, 5000, 6000, 7000, 8000, 9000, 10000, 50000, 100,000 sequencing reactions. In other cases, cell-free poly nucleotides may be sequenced with less than 1000, 2000, 3000, 4000, 5000, 6000, 7000, 8000, 9000, 10000, 50000, 100,000 sequencing reactions. Sequencing reactions may be performed sequentially or simultaneously. Subsequent data analysis may be performed on all or part of the sequencing reactions. In some cases, data analysis may be performed on at least 1000, 2000, 3000, 4000, 5000, 6000, 7000, 8000, 9000, 10000, 50000, 100,000 sequencing reactions. In other cases data analysis may be performed on less than 1000, 2000, 3000, 4000, 5000, 6000, 7000, 8000, 9000, 10000, 50000, 100,000 sequencing reactions. An exemplary read depth is 1000-50000 reads per locus (base).

In some methods, a nucleic acid population is prepared for sequencing by enzymatic blunt-ending of double-stranded nucleic acids with single-stranded overhangs at one or both ends. The population can be treated with a protein with a 5'-3' polymerase activity and a 3'-5' exonuclease activity in the presence of the nucleotides (e.g., A, C, G and T or U). Exemplary proteins are Klenow large fragment and T4 polymerase. At 5' overhangs, the protein extends the recessed 3' end on the opposing strand until it is flush with the 5' end producing a blunt end. At 3' overhangs, the protein digests from the 3' end up to and sometimes beyond the 5' end of the opposing strand. If digestion proceed beyond the 5' end of the opposing strand, the gap can be filled in by polymerase activity as for a 5' overhang. Blunt-ending of double stranded nucleic acids facilitates attachment of adapters and subsequent amplification.

Nucleic acid populations can be subject to additional processing such as conversion of single-stranded nucleic acids to double-stranded and/or conversion of RNA to DNA. These forms of nucleic acid can also be linked to adapters and amplified.

With or without prior amplification, nucleic acids subject to blunt-ending as described above, and optionally other nucleic acids in a sample, can be sequenced to produce sequenced nucleic acids. A sequenced nucleic acid can refer either to the sequence of a nucleic acid or a nucleic acid whose sequence has been determined. Sequencing can be performed so as to provide sequence data of individual nucleic acid molecules in a sample either directly or indirectly from a consensus sequence of amplification products of an individual nucleic acid molecule in the sample.

In some methods, double-stranded nucleic acids with single-stranded overhangs in a sample after blunt-ending are linked at both ends to adapters including barcodes, and the sequencing determines nucleic acid sequences as well as in-line barcodes introduced by the adapters. The blunt-ended DNA molecules can be blunt-end ligated with a blunt end of an at least partially double-stranded adapter (e.g., a Y shaped or bell-shaped adapter). Alternatively, blunt ends of sample nucleic acids and adapters can be tailed with complementary nucleotides to facilitate ligation.

The sample can be contacted with a sufficient number of adapters that there is a low probability (e.g., <1 or 0.1%) that any two instances of the same nucleic acid receive the same combination of adapter bar codes from the adapters linked at both ends. The use of adapters in this manner permits identification of families of nucleic acid sequences with the same start and stop points on a reference nucleic acid and linked to the same combination of barcodes. Such a family represents sequences of amplification products of a nucleic acid in the sample before amplification. The sequences of family members can be compiled to derive consensus nucleotide(s) or a complete consensus sequence for a nucleic acid molecule in the original sample, as modified by blunt ending and adapter attachment. In other words, the nucleotide occupying a specified position of a nucleic acid in the sample is determined to be the consensus of nucleotides occupying that corresponding position in family member sequences. Families can include sequences of one or both strands of a double-stranded nucleic acid. If members of a family include sequences of both strands from a double-stranded nucleic acid, sequences of one strand are converted to their complement for purposes of compiling all sequences to derive consensus nucleotide(s) or sequences. Some families include only a single member sequence. In this case, this sequence can be taken as the sequence of a nucleic acid in the sample before amplification. Alternatively families with only a single member sequence can be eliminated from subsequent analysis.

Nucleotide variations in sequenced nucleic acids can be determined by comparing sequenced nucleic acids with a reference sequence. The reference sequence is often a known sequence, e.g., a known whole or partial genome sequence from an object, whole genome sequence of a human object. The reference sequence can be hG19. The sequenced nucleic acids can represent sequences determined directly for a nucleic acid in a sample, or a consensus of sequences of amplification products of such a nucleic acid, as described above. A comparison can be performed at one or more designated positions on a reference sequence. A subset of sequenced nucleic acids can be identified including a position corresponding with a designated position of the reference sequence when the respective sequences are maximally aligned. Within such a subset it can be determined which, if any, sequenced nucleic acids include a nucleotide variation at the designated position, and optionally which if any, include a reference nucleotide (i.e., same as in the reference sequence). If the number of sequenced nucleic acids in the subset including a nucleotide variant exceeds a threshold, then a variant nucleotide can be called at the designated position. The threshold can be a simple number, such as at least 1, 2, 3, 4, 5, 6, 7, 8, 9, or 10 sequenced nucleic acids within the subset including the nucleotide variant or it can be a ratio, such as a least 0.5, 1, 2, 3, 4, 5, 10, 15, or 20 of sequenced nucleic acids within the subset include the nucleotide variant, among other possibilities. The comparison can be repeated for any designated position of interest in the reference sequence. Sometimes a comparison can be performed for designated positions occupying at least 20, 100, 200, or 300 contiguous positions on a reference sequence, e.g., 20-500, or 50-300 contiguous positions.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the disclosure can be used in combination with any other unless specifically indicated otherwise. Although the present disclosure has been described in some detail by way of illustration and example for purposes of clarity and understanding, it will be apparent that certain changes and modifications may be practiced within the scope of the appended claims.

Examples

This example determines distribution of Z-scores in individuals with various cancer types.

Blood Draw, Shipment, and Plasma Isolation

All cfDNA extraction, processing, and sequencing was performed in a CLIA-certified, CAP-accredited laboratory.

Briefly, for clinical samples, plasma was isolated from 10 ml of whole blood collected in cell-free blood collection tubes by double centrifugation, from which cfDNA was extracted, labeled with non-random barcodes, and 5-30 ng used to prepare sequencing libraries, which were then enriched by hybrid capture, pooled, and sequenced by paired-end synthesis (NextSeq 500 and/or HiSeq 2500, Illumina, Inc.). Contrived analytical samples were generated using similarly prepared cfDNA from healthy donors and cfDNA isolated as above from the culture supernatant of model cell lines and serially size-selected using Agencourt Ampure XP beads (Beckman Coulter, Inc.) until no detectable gDNA remained.

Bioinformatics Analysis and Variant Detection

All variant detection analyses were performed using the locked clinical Guardant360 bioinformatics pipeline and reported unaltered by post-hoc analyses. All decision thresholds were determined using independent training cohorts, locked, and applied prospectively to all validation and clinical samples. As previously described [PMID 26474073], base call files generated by Illumina's RTA software (v2.12) were de-multiplexed using bcl2fastq (v2.19) and processed with a custom pipeline for molecule barcode detection, sequencing adapter trimming, and base quality trimming (discarding bases below Q20 at the ends of the reads). Processed reads were then aligned to hG19 using BWA-MEM [Li et al. 2013 arXiv:1303.3997v2] and used to build double-stranded consensus representations of original unique cfDNA molecules using both inferred barcodes and read start/stop positions. SNVs were detected by comparing read and consensus molecule characteristics to sequencing platform- and position-specific reference error noise profiles determined independently for each position in the panel by sequencing a training set of 62 healthy donors on both the NextSeq 500 and HiSeq 2500. Observed positional SNV error profiles were used to define calling cut-offs for SNV detection with respect to the number and characteristics of variant molecules, which differed by position but were most commonly unique molecules, which in an average sample (5,000 unique molecule coverage) corresponds to a detection limit of ~0.04% allelic fraction. To detect indels, a generative background noise model was constructed to account for PCR artifacts arising frequently in homopolymeric or repetitive contexts, allowing for strand-specific and late PCR errors. Detection was then determined by the likelihood ratio score for observed feature-weighted variant molecule support versus background noise distribution. Reporting thresholds were event-specific as determined by performance in training samples but were most commonly unique molecule for clinically actionable indels, which in an average sample corresponds to a detection limit of ~0.02% allelic fraction. Fusion events were detected by merging overlapping paired-end reads to form a representation of the sequenced cfDNA molecule, which was then, aligned, mapped to initial unique cfDNA molecules based on barcoding and alignment information, including soft clipping. Soft-clipped reads were analyzed using directionality and breakpoint proximity to identify clusters of molecules representing candidate fusion events, which were then used to construct fused references against which reads soft-clipped by the aligner on the first pass were realigned. Specific reporting thresholds were determined by retrospective and training set analyses but were generally unique post-realignment molecules meeting quality requirements, which in an average sample corresponds to a detection limit of ~0.04% allelic fraction. To detect CNAs, probe-level unique molecule coverage was normalized for overall unique molecule throughput, probe efficiency, GC content, and signal saturation and robustly summarized at the gene level. CNA determinations were based on training set-established decision thresholds for both absolute copy number deviation from per-sample diploid baseline and deviation from the baseline variation of probe-level normalized signal in the context of background variation within each sample's own diploid baseline. Per-sample normalized tumor burden was determined by normalization to the mutational burden expected for tumor type and ctDNA fraction and reported as a z-score.

FIG. 1 plots Z-scores for cancer mutation burden in samples from different individuals having one of the cancer types shown on the X-axes. The distribution of Z-scores varies for the different cancer types but is generally asymmetric with the mode generally below zero but with a few individuals showing highly positive Z scores.

What is claimed is:

1. A method of treating a subject having a cancer type or signs of a cancer type, comprising:
   (a) determining a number of mutations present in a test sample of cell-free nucleic acids from the subject and a minor allele fraction based on one or more mutations most highly represented in the test sample of cell-free nucleic acids;
   (b) accessing a dataset containing numbers of mutations in control samples from other subjects with the same cancer type, wherein the dataset is divided into bins according to minor allele fractions of the control samples;
   (c) normalizing the number of mutations present in the test sample to a number of mutations present in control samples within a chosen bin from the dataset having a range of minor allele fractions including the minor allele fraction of the test sample to determine a measure of tumor mutation burden in the test sample;
   (d) determining the measure of tumor mutation burden of the test sample is above a threshold, wherein the threshold is set to provide an indication that a subject will respond positively to immunotherapy; and
   (e) administering one or more agents to effect the immunotherapy to the subject.

2. The method of claim 1, wherein the number of mutations present in the control samples within the chosen bin is an average.

3. The method of claim 1, wherein the chosen bin has a width of no more than 20% of the total variation in minor allele fraction in the dataset.

4. The method of claim 1, wherein the normalizing comprises dividing the number of mutations in the test sample by an average number of mutations in the control samples of the chosen bin.

5. The method of claim 1, wherein the normalizing comprises subtracting from the determined number of mutations in the test sample of cell-free nucleic acids an average of the number of mutations in the control samples of the chosen bin.

6. The method of claim 5, wherein the normalizing comprises dividing the number of mutations in the test sample of cell-free nucleic acids less the average number of mutations present in the control samples of the chosen bin by a standard deviation of the number of mutations present in the control samples of the chosen bin to calculate a Z-score.

7. The method of claim 6, wherein the average is a mean.

8. The method of claim 7, wherein the control samples include at least 25 control samples.

9. The method of claim 7, wherein the control samples include at least 100 control samples.

10. The method of claim 7, wherein the control samples include at least 500 control samples.

11. The method of claim 1, wherein the normalizing comprises determining an average and spread of the number of mutations in at least 10 control samples in the chosen bin, determining a standard score of deviation of the test sample from the average number of mutations and determining whether the standard score is above a threshold number.

12. The method of claim 11, wherein the average of the number of mutations is a mean, median or mode.

13. The method of claim 11, wherein the spread is represented as variance, standard deviation, or interquartile range.

14. The method of claim 11, wherein the standard score of deviation is a Z-score.

15. The method of claim 1, wherein the normalizing further comprises dividing the determined number of mutations in the test sample of cell-free nucleic acids by an average number of mutations present in the control samples of the chosen bin.

16. The method of claim 1, wherein the normalizing is implemented in a computer programmed to store values for the dataset.

17. The method of claim 16, wherein the stored values are a mean and standard deviation of the number of mutations present in the control samples within each of the plurality of bins.

18. The method of claim 1, wherein (a) comprises determining sequences of the cell-free nucleic acids in the test sample and comparing the resulting sequences to corresponding reference sequences to identify the number of mutations present in the sample and the minor allele fraction.

19. The method of claim 18, wherein at least 50,000 nucleotides are sequenced collectively in segments of the cell-free nucleic acids.

20. The method of claim 19, wherein the reference sequences are from hG19 or hG38.

21. The method of claim 1, wherein step (a) comprises determining presence or absence of a panel of predetermined mutations known to occur in cancer of the type present or suspected of being present in the sample.

22. The method of claim 1, wherein step (a) comprises linking adapters to the cell free-nucleic acids, amplifying the cell-free nucleic acids from primers binding to the adapters and sequencing the amplified nucleic acids.

23. The method of claim 1 performed on a plurality of subjects to determine the measure of tumor mutation burden in each subject, wherein a greater proportion of subjects with the measure of tumor mutation burden exceeding the threshold receive immunotherapy for the cancer than subjects with the measure of tumor mutation burden below the threshold.

24. The method of claim 23, wherein all subjects in which the measure is above a first threshold receive immunotherapy and all subjects in which the measure is below a second threshold do not receive immunotherapy.

25. The method of claim 1, wherein the immunotherapy comprises a checkpoint inhibitor antibody.

26. The method of claim 1, wherein the one or more agents to effect the immunotherapy comprises an antibody against PD-1, PD-2, PD-L1, PD-L2, CTLA-40, OX40, B7.1, B7He, LAG3, CD137, KIR, CCR5, CD27, or CD40.

27. The method of claim 1, wherein the cancer type is a solid cancer.

28. The method of claim 1, wherein step (c) comprises determining an average and spread of the number of mutations in at least 50 control samples in the chosen bin, and determining a standard score of deviation of the test sample from the average number of mutations and step (d) comprises determining whether the standard score is above the threshold number.

29. The method of claim 1, wherein step (c) comprises determining an average and spread of the number of mutations in at least 100 control samples in the chosen bin, and determining a standard score of deviation of the test sample from the average number of mutations and step (d) comprises determining whether the standard score is above the threshold.

30. The method of claim 1, wherein step (c) comprises determining an average and spread of the number of mutations in at least 500 control samples in the chosen bin, and determining a standard score of deviation of the test sample from the average number of mutations and step (d) comprises determining whether the standard score is above the threshold number.

* * * * *